United States Patent
Power et al.

(10) Patent No.: US 6,737,412 B2
(45) Date of Patent: May 18, 2004

(54) ANTISENSE OLIGODEOXYNUCLEOTIDES REGULATING EXPRESSION OF TNF α

(75) Inventors: Christopher Power, Calgary (CA); Michael B. Mayne, Winnipeg (CA)

(73) Assignees: Univerisity Technologies International, Inc., Calgary (CA); University of Manitoba, Winnipeg (CA)

( * ) Notice: Subject to any disclaimer, the term of this patent is extended or adjusted under 35 U.S.C. 154(b) by 0 days.

(21) Appl. No.: 09/439,429

(22) Filed: Nov. 15, 1999

(65) Prior Publication Data

US 2003/0083275 A1 May 1, 2003

Related U.S. Application Data

(63) Continuation of application No. 09/176,862, filed on Oct. 22, 1998.
(60) Provisional application No. 60/062,718, filed on Oct. 22, 1997.

(51) Int. Cl.[7] .......................... A61K 31/70; C07H 21/04
(52) U.S. Cl. ...................... 514/44; 536/24.1; 536/24.3; 536/24.31; 536/24.33; 536/24.5
(58) Field of Search .............................. 536/23.1, 24.1, 536/24.3, 24.33, 24.5; 435/6, 325, 375; 514/44

(56) References Cited

U.S. PATENT DOCUMENTS 5,994,315 A * 11/1999 Nyce et al. ................... 514/44

FOREIGN PATENT DOCUMENTS

WO          WO 9410301 A1 *  5/1994

OTHER PUBLICATIONS

Taylor et al. Journal of Biological Chemistry, (1996) vol. 271, No. 29, pp. 17445–17452.*

Ojwang et al. Nucleosides & Nucleotides, (1997) vol. 16(7–9), pp. 1703–1707.*

Hartman et al. Nucleosides & Nucleotides, (1997) vol. 16(5&6), pp. 629–634.*

Crooke, S., Basic Principles of Antisense Therapeutics, Springer–Verlag Berlin Heidelberg New York, Jul. 1998.*

Branch, A., A good antisense molecule is hard to find, TIBS vol. 23, pp. 47–49, Jul. 1998.*

* cited by examiner

Primary Examiner—Sean McGarry
Assistant Examiner—Janet L. Epps-Ford
(74) Attorney, Agent, or Firm—Kohn & Associates, PLLC

(57) ABSTRACT

A synthetic nuclease resistant antisense oligodeoxynucleotide capable of selectively modulating expression of human tumor necrosis factor-alpha by targeting exon sequences flanking donor splice sites, thereby regulating expression of TNF-α in a patient in need of such therapy is provided. In an embodiment either AS—ODN having the sequence set forth in SEQ ID No:4 or SEQ ID No:6 or a combination thereof can be used. The AS—ODN is administered either as the active ingredient in a pharmaceutical composition or by utilizing gene therapy techniques as an expression vector.

6 Claims, 4 Drawing Sheets

ANTISENSE OLIGODEOXYNUCLEOTIDES REGULATING EXPRESSION OF TNF α

CROSS REFERENCE TO RELATED APPLICATIONS

This application claims priority from U.S. Provisional Application No. 60/062,718, filed Oct. 22, 1999. This application is a continuation application of U.S. patent application Ser. No. 09/176,862, filed Oct. 22, 1998.

BACKGROUND OF THE INVENTION

1. Field of the Invention

The present invention provides antisense oligodeoxynucleotides targeted to exon sequences flanking donor splice sites which regulate expression of TNF-α.

2. Description of Related Art

There has been increasing interest in the development of antisense oligodeoxyribonucleotides (AS—ODNs hereinafter) as therapeutic agents and experimental tools (Stein and Cheng, 1993; Wagner, 1994). However, despite the improvement in affinity for target RNA, increased resistance to nucleolytic cleavage, and enhanced delivery of AS—ODNs to cells and their nuclei (Hodges and Crooke, 1995), high concentrations of AS—ODNs continue to be required to inhibit gene expression. To some extent, high AS—ODN concentrations have hampered the development of this technology as an effective pharmacological agent because of cost and non-specific AS-ODN actions.

Many genes encode pre-mRNAs containing introns that are removed by a splicing process that is directed by a complex of small nuclear ribonucleic proteins (snRNPs) called the spliceosome (Staley and Guthrie, 1998). Several reports indicate that gene expression is effectively inhibited by AS—ODNs targeting the intron/exon boundaries of splice sites (Boeve and De Ley, 1994; Dominski and Kole, 1996; Dominski and Kole, 1994; Hodges and Crooke, 1995; Moulds et al., 1995), likely because these domains direct splicing events (Staley and Guthrie, 1998). It has previously been shown in cell free systems that the degree of sequence variability at splice sites influences splicing events (Dominski and Kole, 1994), suggesting that pre-mRNAs with variant splice site sequences would be ideal targets for AS—ODN treatment (Hodges and Crooke, 1995). Since exon sequences upstream of donor (5'), and downstream of acceptor (3') splice sites within pre-mRNA play a critical role in processing RNA (Staley and Guthrie, 1998), it is plausible that these sites encode RNA domains highly susceptible to AS—ODN-mediated inhibition of gene expression. To date, this hypothesis has not been tested systematically in a biologically relevant system such as tumor necrosis factor alpha (TNF-α) production in cell culture or in vivo.

Under normal conditions, TNF-α's expression is tightly regulated by rapid mRNA turnover (Gearing et al., 1995). However, in disease states, its expression is perturbed, resulting in overexpression (Sharief and Hentges, 1991; Tracey and Cerami, 1994). TNF-α is implicated in the pathogenesis of several inflammatory diseases including multiple sclerosis (MS) (French-Constant, 1994), rheumatoid arthritis (RA) (Lupia et al., 1996), viral infections such as human immunodeficiency virus (HIV) (Fauci, 1996) and, bacterial infections causing sepsis (Tomioka et al., 1996). TNF-α neutralizing antibodies (Givner et al., 1995), soluble TNF-α receptors (Moreland et al., 1997), or gene knockouts of the TNF receptor (p55) (Pfeffer et al., 1993) mitigate the harmful effects of TNF-α observed in several animal models of inflammation (Probert et al., 1995; Selmaj et al., 1991). However, these approaches do not limit TNF-α synthesis.

Several studies show that AS—ODNs targeting TNF-α mRNA limit TNF-α synthesis (Hartmann et al., 1996; Lefebvre d'Hellencourt et al., 1996; Rojanasakul et al., 1997; Taylor et al., 1996). However, in these reports, concentrations of AS—ODNs in excess of 2 μM, were required to achieve significant inhibition. High concentrations of AS—ODNs may induce non-specific inflammatory cell responses (Hartmann et al., 1996) as well as other non-specific effects (Gao et al., 1992; Khaled et al., 1996; Perez et al., 1994). Nevertheless, earlier reports suggest that expression of other genes can be regulated by low concentrations (≦1 μM) of AS—ODNs (Hanecak et al., 1996; Miraglia et al., 1996). Therefore it would be useful to develop AS—ODNs that can be used in low concentrations to regulate TNF-α production in inflammatory responses.

SUMMARY OF THE INVENTION

According to the present invention, a synthetic nuclease resistant antisense oligodeoxynucleotide capable of selectively modulating expression of human tumor necrosis factor-alpha by targeting exon sequences flanking donor splice sites, thereby regulating expression of TNF-α in a patient in need of such therapy is provided. In an embodiment either AS—ODN having the sequence set forth in SEQ ID No:4 or SEQ ID No:6 or a combination thereof can be used. The AS—ODN is administered either as the active ingredient in a pharmaceutical composition or by utilizing gene therapy techniques as an expression vector.

DESCRIPTION OF THE DRAWINGS

Other advantages of the present invention will be readily appreciated as the same becomes better understood by reference to the following detailed description when considered in connection with the accompanying drawings wherein:

(FIG. 2A) U937 cells were treated with ORF4 or ORF6 (1 μM, 100 and 10 nM) and supernatant TNF-α levels were measured by ELISA. (FIG. 2B) AS—ODNs are not cytotoxic to U937 cells. Data are presented as a mean±SD (n=3). *($p \leq 0.01$) **($p \leq 0.001$).

(FIG. 4A) U937 cells were treated with ORF4-PE and supernatant TNF-α and IL-6 levels were measured by ELISA. (FIG. 4B) ORF4-PE-mediated inhibition of mitogen-induced TNF-α gene expression in primary human PBMC, macrophages and murine monocytes. PMA/PHA stimulated PBMC produced 1250±110 pg TNF-α/ml/million cells. LPS-stimulated primary macrophages produced 13,500±1,700 pg TNF-α/ml/million cells. LPS-stimulated murine monocytes produced 7,100±875 pg TNF-α/ml/million cells. Data are presented as mean ±SD (n=3). *(p≦0.01)**(p≦0.001).

DETAILED DESCRIPTION OF THE INVENTION

Figure 1:
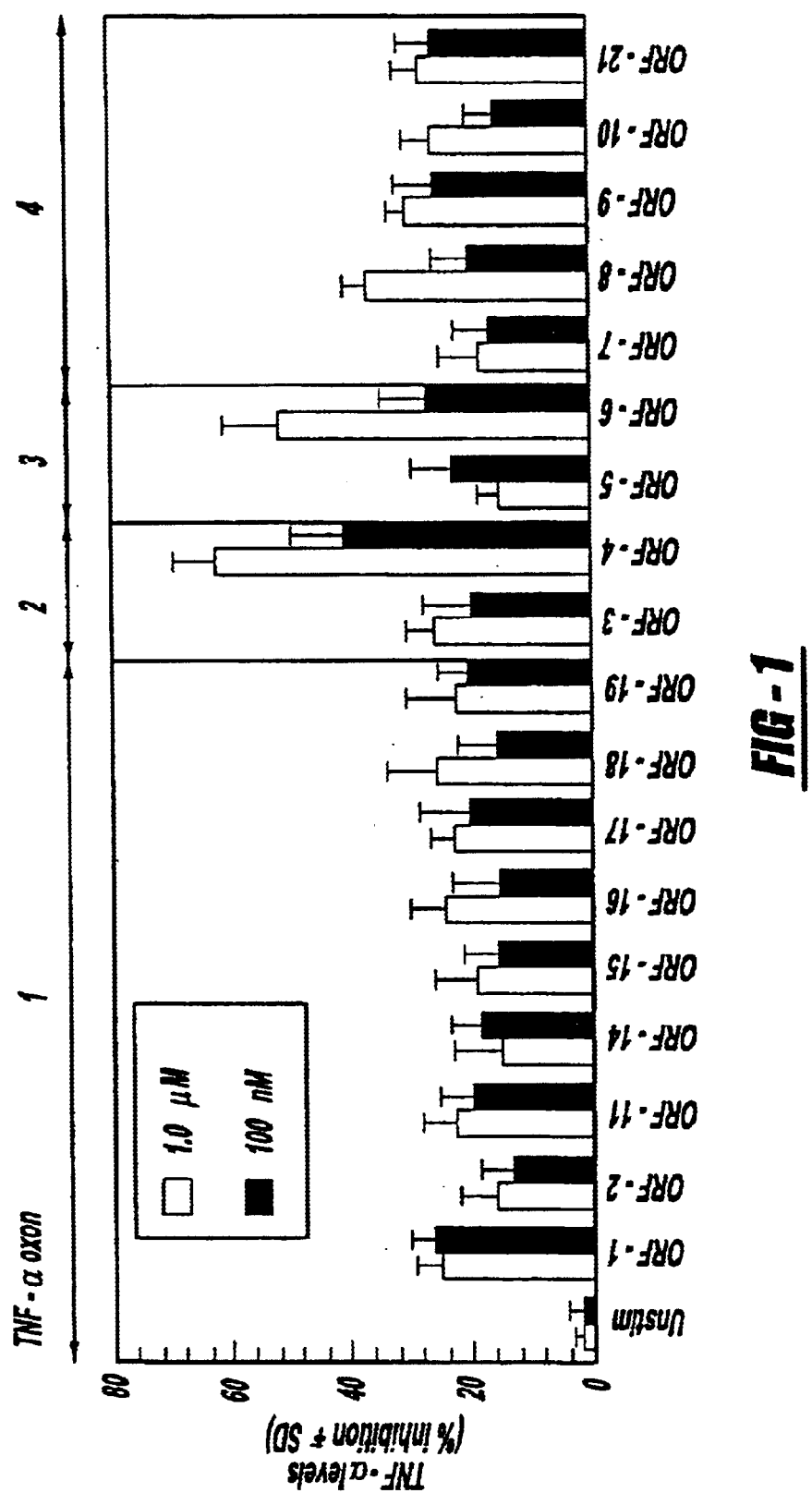
FIG. 1 is a bar graph which shows AS—ODNs targeting exon sequences flanking the donor splice site of exon 2 and 3 of TNF-α effectively inhibit TNF-α protein production. Percent reduction of TNF-α levels in PMA/PHA stimulated U937 cells treated with AS—ODNs targeting various domains within the TNF-α open reading frame. PMA/PHA stimulated U937 cells produced 750±75 pg TNF-α/ml/million cells. * ($p \leq 0.01$)** ($p \leq 0.001$). Unstim—Unstimulated U937 cells; 0-1 through 0-21- ODNs complementary to different sequences of TNF-α. Data are presented as a mean±SD (n=3).

The present invention provides a synthetic nuclease resistant antisense oligodeoxynucleotide (AS—ODN) capable of selectively modulating human tumor necrosis factor alpha (TNF-α) by targeting exon sequences flanking donor splice sites thereby regulating expression of TNF-α in a patient in need of such treatment. Donor splice sites represent the 3' end of an exon and are located at the junction between the exon and intron.

By modulating/regulating it is meant that the expression of TNF-α is inhibited or reduced by the action of the AS—ODNs.

In an embodiment either:

SEQ ID No:4 CTG ACT GCC TGG GCC AGA GGG CTG ATT AG
SEQ ID No:6 CCA CAT GGG CTA CAG GCT TGT CAC TCG can be used or any combination thereof.

As shown in the Example hereinbelow, SEQ ID No:4, when made nuclease resistant by phosphorothioate bonds linking between the four 3'-terminus nucleotide bases, is effective and non-toxic.

Since exon sequences are critical in mRNA processing (Dominski and Kole, 1996; Dominski and Kole, 1994) and genes with short internal exons, such as TNF-α, are highly susceptible to exon skipping (Dominski and Kole, 1991), as shown herein it appears that TNF-α's internal exons encode domain is highly susceptible to AS—ODN actions. As shown herein: (a) the inhibitory action of AS—ODNs targeting TNF-α exon sequences upstream of donor sites and downstream of acceptor sites as well as AS—ODNs that target other regions of the TNF-α gene were determined; (b) stringent criteria in the design and selection of each AS—ODN was used for maximizing its potential efficiency and; (c) AS—ODNs developed by the above criteria are shown effective in different cell types in which TNF-α was stimulated by different signaling pathways. AS—ODNs targeting exon sequences flanking the $2^{nd}$ or $3^{rd}$ exon donor splice sites significantly inhibited TNF-α protein production. Therefor exon sequences flanking donor splice sites of the small internal exons of TNF-α are domains that are highly susceptible to the AS—ODN treatment of the present invention.

The present invention provides pharmaceutical compositions as described hereinbelow and gene therapy means of administering the AS—ODN of the present invention to regulate TNF-α expression. The active ingredient of the pharmaceutical composition is at least one synthetic nuclease resistant antisense oligodeoxynucleotides, or ribozymes, targeting exon sequences flanking donor splice sites, such as SEQ ID No:4 OR SEQ ID No:6 in a physiologically acceptable carrier or diluent. The concentration range of the AS—ODN in the pharmaceutical composition is generally 1.0 µM to 100 nM.

Phosphorothioate antisense oligonucleotides do not normally show significant toxicity and exhibit sufficient pharmacodynamic half-lives in animals [Agarwal et al., 1996]. Antisense induced loss-of-function phenotypes related with cellular development were shown for the glial fibrillary acidic protein (GFAP), for the establishment of tectal plate formation in chick and for the N-myc protein, responsible for the maintenance of cellular heterogeneity in neuroectodermal cultures (ephithelial vs. neuroblastic cells, which differ in their colony forming abilities, tumorigenicity and adherence). Antisense oligonucleotide inhibition of a basic fibroblast growth factor (bFgF), having mitogenic and angiogenic properties, suppressed 80% of growth in glioma cells [Morrison, 1991] in a saturable and specific manner. Being hydrophobic, AS—ODN interact well with phospholipid membranes [Akhter et al., 1991]. Following their interaction with the cellular plasma membrane, they are actively (or passively) transported into living cells [Loke et al., 1989]

The term "oligodeoxynucleotide" refers to an oligomer or polymer of nucleotide or nucleoside monomers consisting of naturally occurring bases, sugars and intersugar (backbone) linkages. The term also includes modified or substituted oligomers comprising non-naturally occurring monomers or portions thereof, which function similarly. Incorporation of substituted oligomers is based on factors including enhanced cellular uptake, or increased nuclease resistance and are chosen as is known in the art. The entire oligodeoxynucleotide or portions thereof may contain the substituted oligomers.

Instead of an antisense sequence, as discussed herein above, ribozymes may be utilized for suppression of gene function. This is particularly necessary in cases where antisense therapy is limited by stoichiometric considerations [Sarver et al., 1990, Gene Regulation and Aids, pp. 305–325]. Ribozymes can then be used that will target the same sequence. Ribozymes are RNA molecules that possess RNA catalytic ability [see Cech for review] and cleave a specific site in a target RNA. The number of RNA molecules that are cleaved by a ribozyme is greater than the number predicted by stochiochemistry. [Hampel and Tritz, 1989; Uhlenbeck, 1987]. Therefore, the present invention also allows for the use of the ribozyme sequences, targeted to exon sequences flanking donor splice sites, which regulate expression of TNF-α expression and contain the appropriate catalytic center. The ribozymes are made and delivered as discussed herein below. The ribozymes may be used in combination with the antisense sequences. Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347, columns 4–5). The latter two families are derived from viroids and virusoids, in which the ribozyme is believed to separate monomers from oligomers created during rolling circle replication. Hammerhead and hairpin ribozyme motifs are most commonly adapted for trans-cleavage of mRNAs for gene therapy (Sullivan, 1994). The ribozyme type utilized in the present invention is selected as is known in the art. Hairpin ribozymes are now in clinical trial and are the preferred type. In general, the ribozyme is from 20–100 nucleotides in length.

Nuclease resistance, where needed, is provided by any method known in the art that does not substantially interfere with biological activity of the antisense oligodeoxynucleotides or ribozymes as needed for the method of use and delivery [Iyer et al., 1990; Radhakrishnan, et al., 1990; Eckstein, 1985; Spitzer and Eckstein, 1988; Woolf et al., 1990; Shaw et al., 1991]. As shown herein in the Example, ORF4-PE (a phosphorothioate derivative of ORF4; SEQ ID No:4) is a preferred embodiment.

Modifications that can be made to antisense oligonucleotides and ribozymes in order to enhance nuclease resistance include modifying the phosphorous or oxygen heteroatom in the phosphate backbone, short chain alkyl or cycloalkyl intersugar linkages or short chain heteroatomic or heterocyclic intersugar linkages. These include preparing methyl phosphonates, phosphorothioates, phosphorodithioates and morpholino oligomers. In one embodiment, it is provided by having phosphorothioate bonds linking some or all the nucleotide bases. Phosphorothioate antisense oligonucleotides do not normally show significant toxicity at concentrations that are effective and exhibit sufficient pharmacodynamic half-lives in animals [Agarwal et al., 1996] and are nuclease resistant. Other modifications known in the art may be used where the biological activity is retained, but the stability to nucleases is substantially increased. The efficiency of inhibition and toxicity can be tested as shown herein in the Example to determine the most effective nuclease resistant protocol.

The nuclease resistant AS—ODNs of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, lower levels of expressed mRNA for TNF-α or improvement or elimination of symptoms and other indicators as are selected as appropriate measures by those skilled in the art. General methods of administration are provided herein which can be modified as known in the art to accommodate the requirements of maintaining and delivery of AS—ODNs.

Once the nuclease resistant oligonucleotide sequences are ready for delivery they can be introduced into cells, as is known in the art. Transfection, electroporation, fusion, liposomes, colloidal polymeric particles and viral vectors, as well as other means known in the art, may be used to deliver the oligonucleotide sequences to the cell. The selected method depends on the cells to be treated and the location of the cells and will be known to those skilled in the art. Localization can be achieved by liposomes, having specific markers on the surface for directing the liposome, by having injection directly into the tissue containing the target cells, by having depot associated in spatial proximity with the target cells, specific receptor mediated uptake, viral vectors, or the like. Transfection vehicles such as liposomes can also be used to introduce the non-viral vectors described above into recipient cells within the inoculated area. Such transfection vehicles are known by one skilled within the art.

The pharmaceutical composition of the present invention may be a combination of the AS—ODNs provided in the present invention. The combination is assembled and dosed as is known in the art. Further, the composition of the present invention may be a combination of one of the AS—ODNs provided in the present invention in combination with at least one other non-control AS—ODN selected from Table 1 or Table 2. This combination would have a low toxicity with a percent inhibition of approximately 25% or more.

The patient being treated is a warm-blooded animal and, in particular, mammals including man. The pharmaceutically acceptable carriers, diluents, adjuvants and vehicles, as well as implant carriers generally refer to inert, non-toxic solid or liquid fillers, diluents or encapsulating material not reacting with the active ingredients of the invention.

It is noted that humans are treated generally longer than the cells exemplified herein which treatment has a length proportional to the length of the disease process and drug effectiveness.

The AS—ODN of the present invention can be administered utilizing gene therapy techniques. Generally, a DNA expression vector comprising an expressible promotor/transcriptional initiator and the AS—ODN sequence is utilized.

"By gene therapy" as used herein refers to the transfer of genetic material (e.g DNA or RNA) of interest into a host to treat or prevent a genetic or acquired disease or condition phenotype. The genetic material of interest encodes a product (e.g. a protein, polypeptide, peptide, functional RNA, antisense) whose production in viva is desired. For example, the genetic material of interest can encode a hormone, receptor, enzyme, polypeptide or peptide of therapeutic value. Alternatively, the genetic material of interest encodes a suicide gene. For a review see, in general, the text "Gene Therapy" (Advances in Pharmacology 40, Academic Press, 1997).

Two basic approaches to gene therapy have evolved: (1) ex vivo and (2) in viva gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ, that is within the recipient. In an alternative embodiment, if the host gene is defective, the gene is repaired in situ [Culver, 1998]. These genetically altered cells have been shown to express the transfected genetic material in situ.

The gene expression vehicle is capable of delivery/transfer of heterologous nucleic acid into a host cell. The expression vehicle may include elements to control targeting, expression and transcription of the nucleic acid in a cell selective manner as is known in the art.

The expression vehicle can include a promotor for controlling transcription of the heterologous material and can be either a constitutive or inducible promotor to allow selective transcription. Enhancers that may be required to obtain necessary transcription levels can optionally be included. Enhancers are generally any non-translated DNA sequence which works contiguously with the coding sequence (in cis) to change the basal transcription level dictated by the promoter. The expression vehicle can also include a selection gene.

Vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene*

Therapy, CRC Press, Ann Arbor, Mich. (1995), Vega et al., *Gene Targeting*, CRC Press, Ann Arbor, Mich. (1995), *Vectors: A Survey of Molecular Cloning Vectors and Their Uses*, Butterworths, Boston Mass. (1988) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neurodegenerative diseases. Following injection, the viral vectors will circulate until they recognize host cells with the appropriate target specificity for infection.

An alternate mode of administration can be by direct inoculation locally at the site of the disease or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes and colloidal polymeric particles can also be used to introduce the non-viral vectors described above into recipient cells within the inoculated area. Such transfection vehicles are known by one skilled within the art.

Many studies show that small incremental differences in TNF-α protein levels have large effects on a variety of biological processes including viral replication (Fauci, 1996), physiological and pathological cell responses to infectious diseases (Beutler and Grau, 1993), cell death (Beutler and van Huffel, 1994; Probert et al., 1997; Talley et al., 1995), and normal cell growth and development (Arvin et al., 1996; Beutler and Grau, 1993; Tracey and Cerami, 1994). Given TNF-α's pivotal role in disease and normal development, complete interruption of TNF-α expression is not desirable. Thus, molecular tools, such as AS—ODNs, which modulate, as opposed to eliminate gene expression, provide optimal gene regulation.

As show herein in the Example, ORF4-PE (a phosphorothioate derivative of ORF4; SEQ ID No:4) significantly reduces TNF-α mRNA levels by greater than 80% and protein levels by approximately 60% in stimulated U937 cells. A greater reduction of TNF-α mRNA compared to protein levels is not unexpected as TNF-α has a short half-life and thus, rapid mRNA turnover (Zheng and Specter, 1996). ORF4-PE was sequence specific, efficacious in different cell types, under different stimulatory conditions and did not influence the gene expression of another proinflammatory cytokine, IL-6. Further study showed that ORF4-PE, alone, does not induce TNF-α expression in U937 or PBMC (data not shown), likely due to the lack of CpG moieties and G quartets which encode domains that may stimulate immune cells (Hartmann et al., 1996; Krieg et al., 1997; Krieg et al., 1996). Thus, the present invention which provides for efficient regulation of TNF-α gene expression can be achieved by using ODNs targeting exon sequences flanking donor sites.

Several reports show a reduction of TNF-α levels in vitro using either an antisense approach (Arima et al., 1997; Hartmann et al., 1996; Lefebvre d'Hellencourt et al., 1996; Liang et al., 1996; Rojanasakul et al., 1997; Taylor et al., 1996; Yang et al., 1993) or a formation of triplex DNA complexes (Aggarwal et al., 1996). However, in these studies, AS—ODN concentrations ranging from 2–20 μM were required to inhibit TNF-α expression. Most studies targeting the highly conserved AUG sequence of TNF-α, assumed that this domain is the most efficient site for interruption of translation. Indeed, this approach indicates that antisense molecules directed at the 5' start region, when efficiently delivered to cells, can effectively reduce TNF-α levels (Rojanasakul et al., 1997). However, a comparison of ORF4-PE with the most efficient TNF-α-specific ODNs reported to date, which targeted the 5' AUG start region (Hartmann et al., 1996; Rojanasakul et al., 1997), showed that ORF4-PE was unexpectedly approximately 2.5-fold more efficacious at reducing TNF-α levels (Table 2). An AS—ODN complementary to the 5' AUG region of TNF-α (ORF1; SEQ ID No:1) was equally inefficient at reducing TNF-α levels (FIG. 1), suggesting that under these experimental conditions, exon sequences upstream of donor splice sites are domains that are highly vulnerable to ODN actions.

The mechanism by which ORF4-PE significantly inhibits TNF-α levels is unclear. ORF4-PE, however, is 100% complementary to the exon sequence (exon #2) flanking the donor splice site and thus, may hybridize with higher efficiency to the exon sequence, compared to the U1 small nuclear ribonucleic acid (snRNA), thereby competitively interrupting spliceosome formation and subsequent splicing (Staley and Guthrie, 1998). An examination of the upstream nucleotide sequence flanking the donor splice site of exon #2 reveals a non-consensus, variant sequence. Encoded within the exon immediately upstream of the donor splice site (3' end of the $2^{nd}$ exon) is the sequence 5'TCA3' whereas the sequence 5' A/C AG3' more frequently occurs at approximately 70, 62 and 80% respectively, at these positions (Hertel et al., 1997; Padgett et al., 1986; Tarn and Steitz, 1997). This same position within the third exon of TNF-α however, is fully conserved which may explain why ORF6, which targets the exon sequence upstream of the donor site flanking exon #3, is less effective than ORF4.

Failure to recognize short internal exons by the spliceosome may be due to juxtaposition of adjacent 3' and 5' splice sites of internal exons, thereby creating steric hindrance and improper spliceosome/splice site interactions (Dominski and Kole, 1991). Both internal exons of TNF-α (exon #2–46 bp and exon #3–48 bp) (accession # M16441: Genbank) are less than 50 bp and thus, may be subject to exon skipping (Dominski and Kole, 1991). Given the rarity of short internal exons in eukaryotic genes (less than 4%) (Hawkins, 1988) and their susceptibility to exon skipping, the addition of competing AS—ODNs would further impede efficient mRNA splicing. In addition, exon skipping can be induced by improper recognition of weak donor splice sites (Dominski and Kole, 1991). Indeed, encoded within the second exon flanking the donor splice site of human TNF-α is a variant sequence that may be competitively inhibited by ORF4-PE. In either event, the exon skipping or direct inhibition of splicing would lead to decreased levels of TNF-α mRNA.

An alternative possibility is that ORF4-PE hybridizes with high affinity to processed mRNA, activating RNase H (Wagner, 1994). Mfold RNA modeling (Jacobson and Zuker, 1993) of human TNF-α mRNA (data not shown) however, shows that the domain complementary to ORF4-PE is predicted to exist as a double stranded structure. Previous studies indicate that double-stranded nucleic acid structures do not provide highly stable targets for antisense AS—ODNs (Lima et al., 1992; Thierry et al., 1993). Thus, although secondary structure of mRNA may limit AS—ODN-mediated actions (Laptev et al., 1994; Mishra et al., 1996; Mishra and Toulme, 1994), it is unexpected to find that ORF4-PE is binding to processed TNF-α mRNA and therefore activating RNase H.

Finally, although Lipofectin was found to decrease TNF-α production in U937 cells by approximately 15%, use of this carrier significantly increased the efficiency of ORF4, ORF4-PE and ORF6. These studies indicated that all AS—ODNs required a final positive net charge (as determined by the ratio of Lipofectin to ODN (Lappalainen et al., 1997) in order to effectively reduce gene expression. Specifically, Lipofectin concentrations of 10, 5 and 1 μg/ml were mixed with ORF4 (1 μM) with 10 μg of Lipofectin having the highest degree of efficiency (data not shown). These findings are similar to previous reports of Lipofectin-enhanced cellular uptake of AS—ODNs (Hartmann et al., 1996; Lappalainen et al., 1997; Zelphati and Szoka, 1996).

These studies demonstrate that exon sequences upstream of donor splice sites within small internal exons of a naturally occurring gene, constitute domains that are highly susceptible to AS—ODN-mediated inhibition of gene expression. In addition, a highly efficient antisense AS—ODN, ORF4-PE (SEQ ID No:4), was designed which is useful in vitro and in vivo in models which study TNF-α dysregulation as well as therapeutically.

The above discussion provides a factual basis for the use of AS—ODNs that can be used in low concentrations to regulate TNF-α production in inflammatory responses. The methods used with and the utility of the present invention can be shown by the following non-limiting examples and accompanying Figures and Tables.

EXAMPLES

Methods:

General methods in molecular biology: Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., Recombinant DNA, Scientific American Books, New York and in Birren et al (eds) *Genome Analysis: A Laboratory Manual Series*, Vols. 1–4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al.(eds), Basic and Clinical Immunology (8th Edition), Appleton & Lange, Norwalk, Conn. (1994) and Mishell and Shiigi (eds), Selected Methods in Cellular Immunology, W. H. Freeman and Co., New York (1980).

Immunoassays In general, ELISAs as described herein are employed to assess the TNF-α levels. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989.

Cell culture and primary cell preparations. The human promonocytic cell line, U937 was obtained from American Type Culture Collection, (ATCC CRL 1593.2; batch F12641) (12301 Parklawn Drive, Rockville, Md. 20852, USA) and was cultured as previously outlined (Chen et al., 1997). Murine monocyte cells, IC-21 (ATCC TIB 186) were maintained at an approximate density of $2.0\times10^5$ cells/ml in 10 mM HEPES buffered, RPMI media supplemented with 10% FBS. Human peripheral blood mononuclear cells (PBMC) and macrophages were purified from whole blood obtained from healthy volunteers as previously outlined (Power et al., 1995). Briefly, to obtain primary human macrophages, PBMC were cultured for 3 d. in RPMI 1640 media supplemented with 20% heat-inactivated FBS and 50 units of penicillin and 50 μg of streptomycin/L. Non-adhering cells were removed by washing with RPMI media and adhering monocytic cells were removed and cultured at a density of $2.0\times10^5$ cells/ml for seven days in RPMI supplemented with 20% FBS and antibiotics. All cells were maintained at 37° C. in a humidified growth chamber supplemented with 5% $CO_2$.

Design and synthesis of AS—ODNs. AS—ODNs were generated using the computer DNA modeling program PrimerSelect (DNASTAR) which designs AS—ODNs based on optimal free energy (Δ G), low dimer formation, low hairpin formation and high thermal stability. AS—ODNs were designed to target exon sequences upstream of the donor (5') and downstream of the acceptor (3') splice sites and other regions throughout the open reading frame (ORF) of human TNF-α (accession # M10988: GenBank) and were assessed for sequence similarity with other non-TNF-α mRNAs (GenBank). TNF-α mRNA numbering was defined such that A in the AUG start codon was position +1. AS—ODNs were chosen if they met the following requirements: size between 16 and 30 mer; low hairpin formation (≦3 base pairs); low dimer formation (≦3 consecutive bases) and melting temperatures above 45° C. All AS—ODNs were synthesized using standard phosphoramidite methods at 0.05 or 0.2 μmol scales and were HPLC purified by the manufacturer (Life Technologies, Mississauga, ONT).

Cell culture stimulation and AS—ODN treatment. Immortalized monocytic cells (U937 (human) or IC-21 (murine)) were cultured to approximately 80% confluency and were seeded at a density of 400,000 cells/ml (U937) or 200,000 cells/ml (IC-21) in a 96 well plate in OPTI-MEM serum reduced media (pH 7.4) supplemented with 5% FBS without antibiotics. Human PBMC were seeded at a density of 500,000 cells/ml. Serum levels were reduced to 5% as recommended for Lipofectin use by the manufacturer. AS—ODNs (1 µM, 100 and 10 nM) were mixed with Lipofectin (10 µg/ml) (Life Technologies, Mississauga, Ontario, Canada) and added to the cell cultures for three hours. The cells were subsequently stimulated for 1 h with 10 ng/ml of phorbol-12-myristate-13-acetate (PMA) and 5 µg/ml phytohemagglutinin (PHA). The cells were then washed once with OPTI-MEM media supplemented with 5% FBS. AS—ODN/Lipofectin mixtures equal to the initial dosage were then added to each respective well. Since stimulated macrophages display maximum TNF-α mRNA levels at 3 hours, and protein formation at 3 to 4 hours (Zheng and Specter, 1996), all cells treated with AS—ODNs were incubated for 4 hours at 37° C. and supernatants were collected, centrifuged at 700× g for 5 minutes and analyzed for TNF-α by ELISA. To determine AS—ODN cytotoxicity, U937 cells were treated with 5, 1, and 0.1 µM of AS—ODNs. AS—ODN-mediated cell death was determined both in the presence and absence of Lipofectin by measuring cell proliferation and viability (as measured by trypan blue exclusion) at 4, 8, and 24 hours. All antisense screening experiments were performed in triplicate, a minimum of three times.

LPS treatment of primary macrophages. Primary macrophage cultures (200,000 cells/ml) were maintained in complete RPMI media supplemented with 20% FBS and antibiotics for 7 days following purification. Cell cultures were washed once with RPMI media and then suspended in OPTI-MEM serum-reduced media supplemented with 5% FBS the day prior to the experiment. Macrophage cultures were treated with Lipofectin-delivered AS—ODNs for 3 hours, washed once with OPTI-MEM media supplemented with 5% FBS and stimulated for 1 hour with 1 µg/ml lipopolysaccharide (LPS) (E. coli type 055:B5) (Sigma) and AS—ODNs were administered as outlined above. Following 4 hours incubation, the supernatants were collected and analyzed by ELISA.

Quantitative immunoassay for cytokines. TNF-α levels in tissue culture supernatants were determined by a sandwich ELISA as previously reported (Chen et al., 1997). Human IL-6 and murine TNF-α levels were quantified using sandwich ELISA according to the manufacturer (Pharmingen). Serial doubling dilutions of human or murine recombinant TNF-α (1250 to 4.5 pg/ml) or IL-6 (2500 to 19.5 pg/ml) was used to generate standard curves. For all experiments, values are corrected for the presence of Lipofectin and are presented as mean±SD (n=3).

Total RNA extraction and RT-PCR. Total cellular RNA was prepared from approximately 1×10$^6$ cells as previously described (Gough, 1988). Pilot studies were performed comparing different PCR cycle number and input RNA concentrations to ensure linear amplification of template occurred. RT-PCR amplification was within linear range when 2 µg of total RNA was reverse transcribed into cDNA (Pharmacia, Mississauga, ONT) followed by PCR amplification of 2 µl of cDNA product using either TNF-α or GAPDH cDNA specific primers (Chen et al., 1997; Wesselingh et al., 1993) for 25 cycles at 95° C. denaturation (60 s), 60° C. annealing (60 s) and 72° C. extension (60 s). These conditions confirmed previous findings by applicants (Chen et al., 1997; Wesselingh et al., 1993). Products were separated by agarose gel electrophoresis (1.4%), transferred to a nylon membrane and probed using a randomly labeled $^{32}$P-dCTP human TNF-α cDNA (Wang et al., 1985) or human GAPDH (Chen et al., 1997). Densiometric analysis of RT-PCR products was performed using the public domain program NIH Image (Ver 1.60).

Statistical analysis. Results were statistically analyzed by two-tailed Student's t-test.

Results

Exon sequences immediately upstream of donor splice sites of TNF-α are highly susceptible to AS—ODN-mediated inhibition. Recent evidence suggests that TNF-α production can be regulated by antisense AS—ODNs, however, AS—ODN concentrations ranging from 2–20 µM are required to reduce TNF-α levels in cells (Hartmann et al., 1996; Lefebvre d'Hellencourt et al., 1996; Rojanasakul et al., 1997; Taylor et al., 1996). At a concentration of 1 µM or less, applicants examined the efficiency of AS—ODNs targeting exon sequences upstream of donor sites and downstream of acceptor splice sites as well as other regions within the TNF-α mRNA (Table 1). These studies unexpectedly show that AS—ODNs targeting exon sequences upstream of the donor splice site of exon 2 (ORF4; SEQ ID No:4) and 3 (ORF6; SEQ ID No:6) reduced TNF-α levels in PMA/PHA stimulated U937 cells (FIG. 1, Table 1). TNF-α levels in stimulated U937 cells were reduced by 62±7% (p<0.001) by ORF4 (SEQ ID No:4) and 51 ±9% (p<0.005) by ORF6 (SEQ ID No:6) (FIG. 1, Table 1). In contrast, AS—ODNs targeting exon sequences downstream of the acceptor sites of exon 2 (ORF3; SEQ ID No:3) and 3 (ORF5; SEQ ID No:5) or AS—ODNs targeting other TNF-α mRNA domains, including the 3' UTR UA rich region did not significantly reduce TNF-α levels (FIG. 1, Tables 1, 2). AS—ODNs designed to complement the 5' AUG start site of human TNF-α (Rojanasakul et al., 1997) were not as efficacious as ORF4 (SEQ ID No:4) or ORF6 (SEQ ID No:6) under the same conditions (FIG. 1, Table 1) and mismatched versions of ORF4 (n=2) did not significantly inhibit TNF-α production (Table 1). In addition, a 21 mer AS—ODN, O-8433 (SEQ ID No:23) that targets the HIV-1 tat gene, was used to assess for non-specific AS—ODN effects. O-8433 did not significantly affect supernatant TNF-α levels in stimulated U937 cells (Table 1).

Figure 2A:
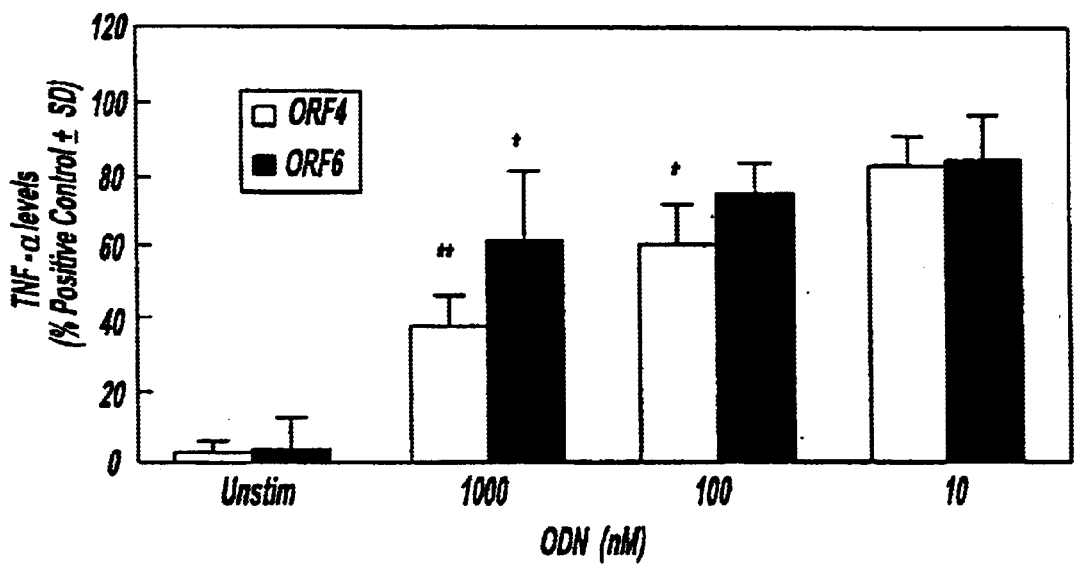
FIGS. 2A–B are bar graphs which show ORF4 (SEQ ID No:4) and ORF6 (SEQ ID No:6) reduce TNF-α production in a dose-dependent manner.

Since ORF4 and ORF6 displayed the greatest inhibition of TNF-α synthesis, these antisense oligonucleotide molecules were further analyzed. In addition to 1 µM of ORF4 and ORF6 significantly reducing TNF-α levels, 100 and 10 nM of ORF4 reduced levels by 40±9% and 19±7% respectively and 100 and 10 nM of ORF6 reduced TNF-α levels by 26±8% and 18±9% respectively (FIG. 2a).

Figure 2B:
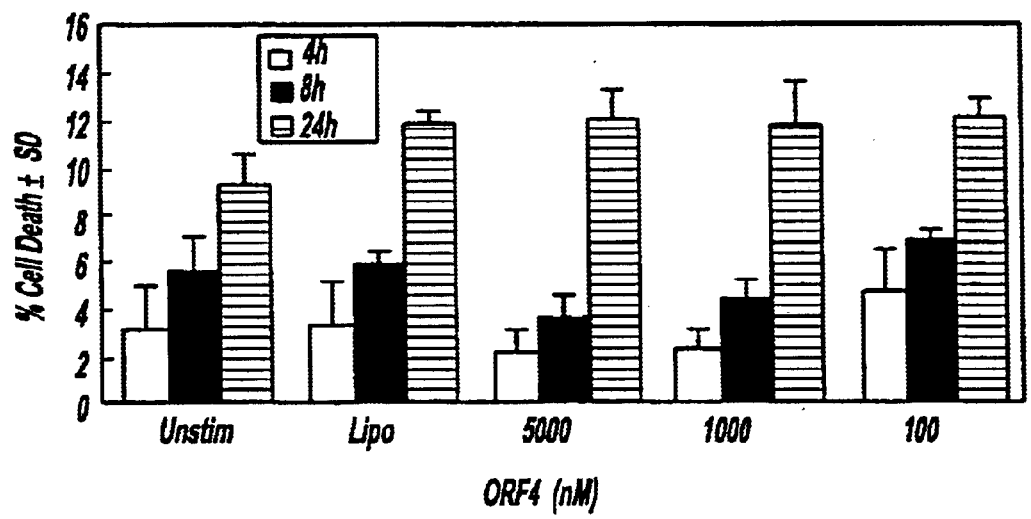

To ensure that 1 µM concentrations of AS—ODN were not toxic to U937 cells, AS—ODN concentrations as high as 5 µM were added to U937 cells which were subsequently tested for proliferation and viability. Five µM ORF4 had no effect on cell proliferation or viability at 4, 8 or 24 hours (FIG. 2b). Cells treated with AS—ODNs delivered by Lipofectin showed similar results up to 24 hours. After 24 hours treatment however, Lipofectin-treated cells showed significant cell death, presumable due to Lipofectin cytotoxicity (Bell et al., 1998; Yagi et al., 1993) (data not shown).

Detailed analysis of AS—ODNs targeting exon sequences flanking donor and acceptor splice sites. Since AS—ODNs complementary to the exon sequences upstream of the donor splice site of exons 2 and 3 of TNF-α significantly inhibited TNF-α production, adjacent nucleic acid domains of the exons were examined in greater detail (Table 2). Specifically, AS—ODNs (n=10) were designed to target regions spanning the small internal exons (exons 2 and 3) of human TNF-α. All AS—ODNs were partially phosphorothioated (approximately 30%) and ORF4 (SEQ ID No:4) was partially phosphorothioated (ORF4-PR) or phosphorothioated at 3 bases on each end of ORF4 (SEQ ID No:4, ORF4-PE) in order to increase nuclease stability (Table 1) (Uhlmann et al., 1997). Only AS—ODNs targeting exon sequences upstream of the donor splice site, independent of their size, significantly reduced TNF-α production (Table 2). Conversely, AS—ODNs targeting the downstream exon sequences of the acceptor site did not reduce TNF-α levels to the same extent. Of all AS—ODNs tested in U937 cells, ORF4-PE was the most efficacious (65±5%) (Table 2). In contrast, ORF4-PR, which was randomly phosphorothioated throughout its 29 mer sequence, reduced TNF-α levels by 42±5% which was significantly less (p<0.001) than ORF4-PE (Table 2) suggesting that site(s) of phosphorothioation may be critical determinants of AS—ODN efficiency.

Figure 3:
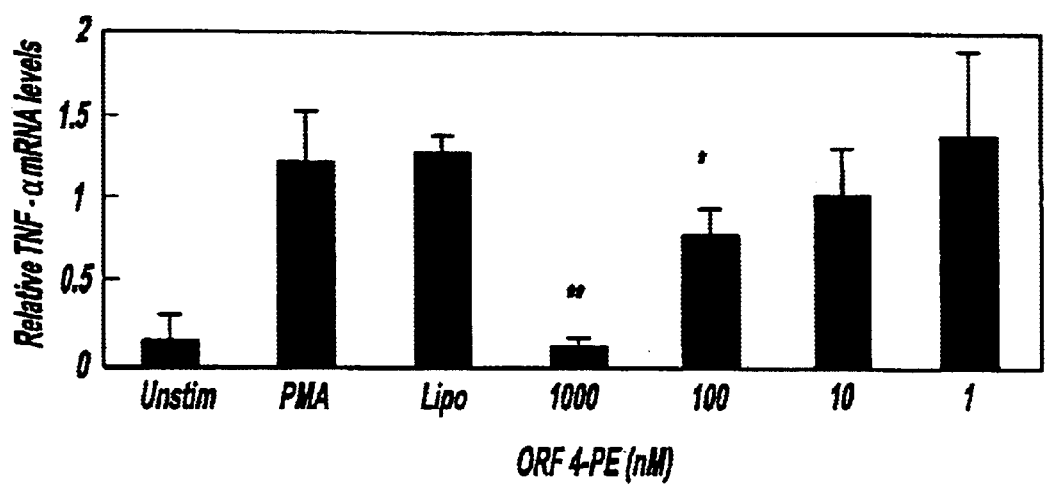
FIG. 3 is a bar graph which shows ORF4-PE dose-dependently reduces TNF-α mRNA in stimulated U937 cells. RT-PCR was used to detect TNF-α and GAPDH mRNA levels in U937 cells treated with ORF4-PE. Densiometric analysis of TNF-α RT-PCR products from U937 cells treated with ORF4-PE. Relative TNF-α mRNA levels were calculated based on the pixel density ratio of TNF-α:GAPDH PCR product in each separate reaction. Data are presented as a mean±SD (n=3). *($p \leq 0.05$)**($p \leq 0.01$).

ORF4-PE (SEQ ID No:4) dose-dependently reduces TNF-α mRNA levels in stimulated U937 cells. To determine the extent to which ORF4-PE influenced TNF-α mRNA levels RT-PCR was performed using primers that amplified a segment of TNF-α spanning exons 2, 3 and 4. RT-PCR products, confirmed by Southern analysis, showed that ORF4-PE dose-dependently reduced the levels of the correctly processed TNF-α mRNA. Densiometric analysis of RT-PCR products confirmed that as the concentration of ORF4-PE increased, TNF-α mRNA detection decreased (FIG. 3). Interestingly, an additional RT-PCR product, smaller than expected (430 bp), was present in samples treated with 1 µM ORF4-PE (data not shown). Although the source of this PCR product is unknown, this band may be the result of a cryptic splicing event (Hodges and Crooke, 1995). However, larger intermediary RNA species were not observed, perhaps due to rapid degradation of improperly spliced pre-mRNA (Khoury et al., 1979).

Figure 4A:
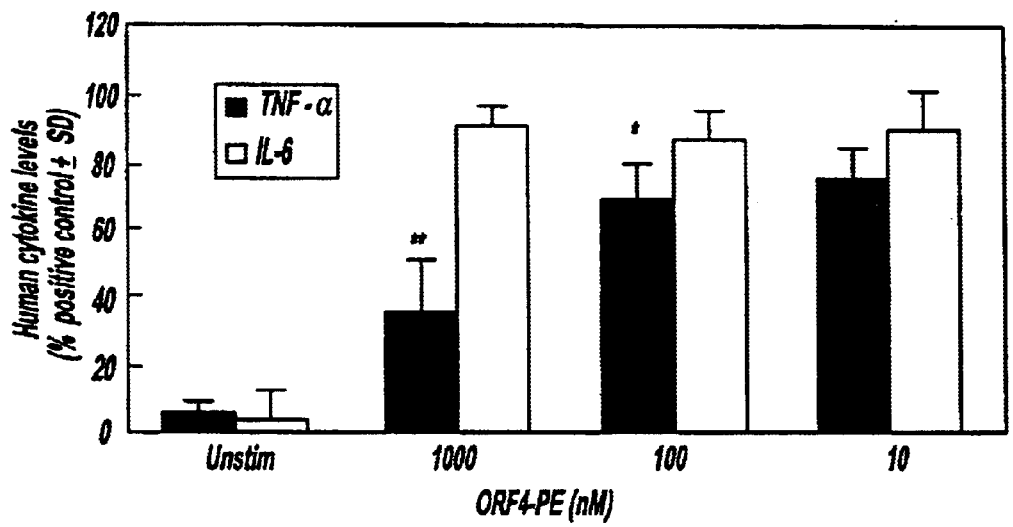
FIGS. 4A–B are bar graphs which show ORF4-PE specificity for TNF-α.

ORF4-PE (SEQ ID No:4) efficiency in U937, human PBMC and primary macrophages and immortalized murine monocytes. Since phosphorothioation of the end sequences of ORF4-PE did not impede its efficiency in stimulated U937 cells, this antisense molecule was used in all subsequent experiments. Phosphorothioation of ORF4 could potentially introduce non-specific effects (Hartmann et al., 1996), therefore, the specificity of ORF4-PE was further analyzed. ORF4-PE (5 µM), in the absence of Lipofectin, was not toxic to U937 cells (data not shown) and displayed a dose response similar to that of ORF4 where 1 µM, 100 and 10 nM reduced TNF-α levels in stimulated U937 cells by 65±5%, 36±7% and 23±8% respectively (FIG. 4a). To determine whether ORF4-PE influenced other inflammatory cytokine levels, IL-6 levels were measured in supernatants from stimulated U937 cells treated with ORF4-PE. ORF4-PE doses of 1 µM, 100 and 10 nM did not significantly affect IL-6 levels in the supernatants of stimulated U937 cells (FIG. 4a).

Figure 4B:
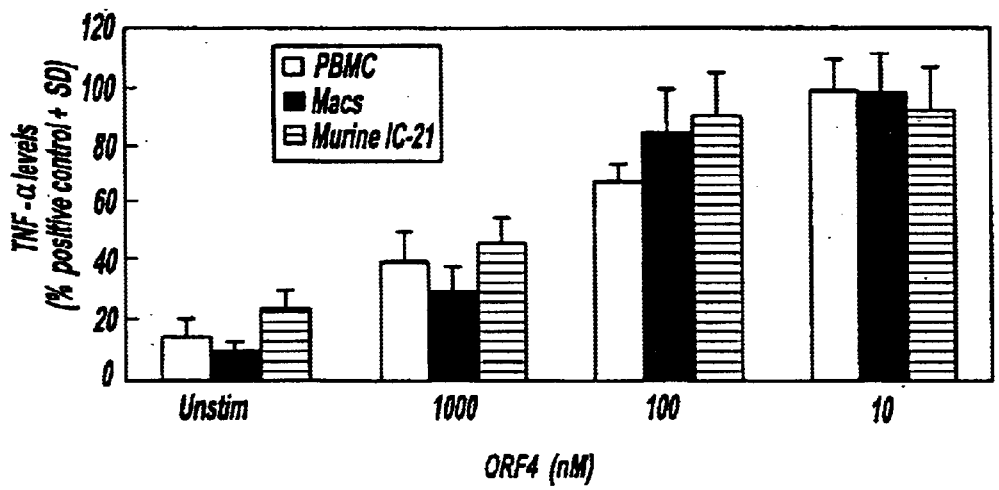

To determine the efficiency of ORF4-PE in primary human cells under different stimulatory conditions, primary cells were treated with ORF4-PE and stimulated with PMA/PHA (10 ng/5 µg/ml; PBMC) or with LPS (1 µg/ml; macrophages). ORF4-PE (1 µM) treatment of PBMC cultures significantly decreased PMA/PHA TNF-α gene expression by 62±9% (p<0.001) (FIG. 4b). ORF4-PE (1 µM) treatment of LPS-stimulated primary macrophages significantly decreased TNF-α levels by 73±8% (p<0.00004)(FIG. 4b). In both PBMC and primary macrophages, 100 and 10 nM ORF4-PE showed a trend of dose-dependent reduction of TNF-α levels (FIG. 4b). All PBMC (n=5) and primary macrophage cultures (n=5), were susceptible to ORF4-PE treatment with inhibition of TNF-α ranging approximately from 50 –70% in PBMC cultures and from 70–85% in primary macrophages (data not shown). ORF4-PE efficiency of TNF-α reduction was approximately 10–15% greater in primary macrophage cultures compared to PBMC or U937 cells, possibly due to active AS—ODN/Lipofectin phagocytosis by primary macrophages (Chaudhuri, 1997; Iversen et al., 1992). Finally, since the TNF-α gene sequence is highly conserved across species, the relative cross-species efficiency of ORF4-PE was tested in murine monocytes treated with ORF4-PE and stimulated with LPS. ORF4-PE (1 µM) significantly reduced murine TNF-α levels in LPS-stimulated cells by 48±8% (p<0.009) (FIG. 4b). Thus, in both human and murine cells, exon sequences upstream of the donor splice site of the $2^{nd}$ exon of TNF-α are highly susceptible to AS—ODN actions.

In summary, exon sequences upstream of splice sites play a critical role in mRNA processing. Correct mRNA processing is dependent on spliceosome interactions with these sites. Using antisense oligodeoxynucleotides (AS—ODNs), these and other sequences of the proinflammatory tumor necrosis factor alpha (TNF-α) gene were targeted because it is multiply spliced and has been difficult to regulate with AS—ODNs in the past. AS—ODNs targeting exon sequences upstream of the donor splice sites of internal exons 2 (ORF4) and 3 (ORF6) significantly reduced TNF-α levels in stimulated U937 cells by 62±7% and 51±9%, respectively, in a dose-dependent manner but did not affect IL-6 levels (see Tables). In contrast, AS—ODNs targeting the exon sequences downstream of the acceptor splice sites of exon 1, 2 and 3 failed to reduce TNF-α levels significantly under the same conditions. End-phosphorothioated ORF4 (ORF4-PE) significantly reduced TNF-α mRNA levels by greater than 80% (p<0.001) and protein levels by 60% (p<0.001) in U937 cells. ORF4-PE reduced newly synthesized TNF-α protein levels by greater than 80% in LPS-stimulated human macrophages, by greater than 60% in PMA/PHA-stimulated human PBMC and by approximately 50% in LPS-stimulated murine monocytes. These results show that exon sequences flanking donor splice sites provide highly vulnerable target domains for antisense inhibition of TNF-α gene expression.

Throughout this application, various publications, including United States patents, are referenced either by number or by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

ODN sequence, target domain and % inhibition of TNF-α.

| AS-ODN | Sequence[1]/SEQ ID No: | Mer | TNF-α Position[2] | % inhibition[3] (mean ± SD) |
|---|---|---|---|---|
| ORF1 | GCC AGC TCC ACG TCC CGG ATC ATG CTT TCA  SEQ ID No:1 | 30 | +9–+38 | 25 ± 5 |
| ORF2 | GGC TGA GGA ACA AGC ACC GCC TGC AG  SEQ ID No:2 | 26 | +78–+103 | 16 ± 6 |
| ORF3 | GAC TCT TCC CTC TGG GGG CCG ATC ACT CCA  SEQ ID No:3 | 30 | +159–+188 | 25 ± 5 |
| ORF4 | CTG ACT GCC TGG GCC AGA GGG CTG ATT AG  SEQ ID No:4 | 29 | +205–+233 | 62 ± 7** |
| ORF5 | TCG GGG TTC GAG AAG ATG ATC TGA CTG C  SEQ ID No:5 | 28 | +226–+253 | 14 ± 4 |
| ORF6 | CCA CAT GGG CTA CAG GCT TGT CAC TCG  SEQ ID No:6 | 27 | +251–+277 | 51 ± 9* |
| ORF7 | GCT TGA GGG TTT GCT ACA ACA TGG GCT ACA  SEQ ID No:7 | 30 | +264–+293 | 18 ± 6 |
| ORF8 | GGC CCG GCG GTT CAG CCA CTG GAG  SEQ ID No:8 | 24 | +304–+327 | 36 ± 4 |
| ORF9 | CAC GCC ATT GGC CAG GAG GGC ATT GG  SEQ ID No:9 | 26 | +326–+351 | 30 ± 3 |
| ORF10 | AGG TAC AGG CCC TCT GAT GGC ACC ACC AG  SEQ ID No:10 | 29 | +370–+398 | 25 ± 5 |
| ORF11 | CCT GTC TTC TTG GGG AGC GCC TCC TC  SEQ ID No:11 | 26 | +40–+65 | 22 ± 6 |
| ORF14 | CTG GGG CCC CCC TGT CTT CTT GGG GA  SEQ ID No:12 | 26 | +50–+75 | 15 ± 8 |
| ORF15 | GCC TGG AGC CCT GGG GCC CCC CTG TC  SEQ ID No:13 | 26 | +60–+85 | 19 ± 7 |
| ORF16 | ACA AAG CAC CGC CTG GAG CCC TGG GG  SEQ ID No:14 | 26 | +70–+95 | 24 ± 6 |
| ORF17 | GGA AGG AGA AGA GGC TGA GGA ACA  SEQ ID No:15 | 24 | +92–+115 | 22 ± 5 |
| ORF18 | TGC CAC GAT CAG GAA GGA GAA  SEQ ID No:16 | 21 | +106–+126 | 25 ± 8 |
| ORF21 | GCA GCA GGA AGA AGA GCG TGG TG  SEQ ID No:17 | 23 | +132–+154 | 28 ± 4 |
| O-3'UTR | AAT AAT AAA TAA ATA ATA AAT AAT CAC AAG  SEQ ID No:18 | 31 | +1310–+1339 | 21 ± 5 |
| ODN 5'A[5] | CAT GCT TTC AGT CAT  SEQ ID No:19 | 15 | 5'AUG start | 26 ± 8 |
| ODN 5'B[6] | TGT GCT CAT GGT GTC TTT  SEQ ID No:20 | 18 | 5'AUG start | 27 ± 9 |
| Controls | | | | |
| ORF4MM1[4] | CTG ACA TCC TGC GCC CCA GGG CTG ATT AG  SEQ ID No:21 | 29 | +205–+233 | 22 ± 9 |
| ORF4MM2[4] | CTG ACT GCC TGC TCC AGA GGG CTG ATT  SEQ ID No:22 | 27 | +207–+233 | 28 ± 8 |

TABLE 1-continued

ODN sequence, target domain and % inhibition of TNF-α.

| AS-ODN | Sequence[1]/SEQ ID No: | Mer | TNF-α Position[2] | % inhibition[3] (mean ± SD) |
|---|---|---|---|---|
| O-8433 | ATC GTC CGG ATC TGT CTC TGT SEQ ID No:23 | 21 | HIV-1 Tat | 19 ± 4 |

[1]Antisense ODN sequences are shown in a 5' to 3' direction.
[2]Positions are numbered relative to the 5' AUG sequence of TNF-α.
[3]U937 cells were treated with 1 μM ODN and percent inhibition of TNF-α was corrected for the presence of Lipofectin.
[4]Mismatches of bases within ORF4 are denoted in bold.
[5]Hartmann et al. 1996.
[6]Rojanasakul et al. 1997
** ($p \leq 0.001$).

TABLE 2

ODNs sequence, target site within the second or third exon and % inhibition of TNF-α.

| AS-ODN | Sequence[1]/SEQ ID No: | Mer | TNF-α position[2] | Flanking[3] splice site | % inhibition[4] (mean ± SD) |
|---|---|---|---|---|---|
| | | | exon 2 | | |
| ORF4-PE | CTG ACT GCC TGG GCC AGA GGG CTG ATT AG SEQ ID No:4 | 29 | +205→+233 | donor | 65 ± 5** |
| ORF4-PR | CTG ACT GCC TGG GCC AGA GGG CTG ATT AG SEQ ID No:4 | 29 | +205→+233 | donor | 42 ± 5* |
| 04.5 | GAT TAG AGA GAG GTC CCT GGG SEQ ID No:24 | 21 | +190→+210 | acceptor | 32 ± 6 |
| 04.10 | TGG GCC AGA GGG CTG A SEQ ID No:25 | 16 | +209→+224 | mid exon | 31 ± 7 |
| 04.4 | AGG GCT GAT TAG AGA GAG GTC SEQ ID No:26 | 21 | +195→+216 | mid exon | 31 ± 8 |
| 04.1 | TGC CTG GGC CAG AGG GCT GAT TAG SEQ ID No:27 | 24 | +205→+228 | donor | 43 ± 5* |
| 04.2 | CTG ACT GCC TGG GCC AGA GGG CTG SEQ ID No:28 | 24 | +210→+233 | donor | 42 ± 4* |
| 04.3 | ACT GCC TGG GCC AGA GGG CTG SEQ ID No:29 | 21 | +210→+230 | donor | 39 ± 5* |
| 04.7 | TTC GAG AAG ATG ATC TGA CTG SEQ ID No:30 | 21 | +227→+247 | donor | 44 ± 8* |
| | | | exon 3 | | |
| 04.6 | GAA GAT GAT CTG ACT GCC TGG SEQ ID No:31 | 21 | +222→+242 | acceptor | 28 ± 4 |
| 04.8 | GGG GTT CGA GAA GAT GAT SEQ ID No:32 | 18 | +233→+251 | acceptor | 34 ± 5 |
| 04.9 | CTT GTC ACT CGG GGT TCG SEQ ID No:33 | 18 | +244→+261 | mid exon | 32 ± 4 |

[1]Antisense ODN sequences are shown in a 5' to 3' direction. Phosphorothioated nucleotides are denoted in bold font.
[2]Positions are numbered relative to the 5' AUG sequence of TNF-α.
[3]ODNs were designed to target exon sequences flanking donor or acceptor sites of the internal exons of TNF-α.
[4]U937 cells were treated with 1 μM ODN and % inhibition of TNF-α was corrected for the presence of Lipofectin.
* ($p \leq 0.01$)**($p \leq 0.001$).

REFERENCES

Aggarwal, B. B., Schwarz, L., Hogan, M. E., and Rando, R. F. (1996). Triple helix-forming oligodeoxyribonucleotides targeted to the human tumor necrosis factor (TNF) gene inhibit TNF production and block the TNF-dependent growth of human glioblastoma tumor cells. Cancer Res 56, 5156–5164.

Agrawal, 1996. Antisense oligonucleotides: towards clinical trials, TIBTECH, 14:376.

Arima, H., Aramaki, Y., and Tsuchiya, S. (1997). Effects of oligodeoxynucleotides on the physicochemical characteristics and cellular uptake of liposomes. J Pharm Sci 86, 438–442.

Arvin, B., Neville, L. F., Barone, F. C., and Feuerstein, G. Z. (1996). The role of inflammation and cytokines in brain injury. Neurosci Biobehav Rev 20, 445–452.

Bell, H., Kimber, W. L., Li, M., and Whittle, I. R. (1998). Liposomal transfection efficiency and toxicity on glioma cell lines: in vitro and in vivo studies. Neuroreport 9, 793–798.

Beutler, B., and Grau, G. E. (1993). Tumor necrosis factor in the pathogenesis of infectious diseases. Crit Care Med 21, S423–435.

Beutler, B., and van Huffel, C. (1994). Unraveling function in the TNF ligand and receptor families. Science 264, 667–668.

Boeve, C. M., and De Ley, M. (1994). Inhibition of human interferon-gamma expression by antisense oligodeoxynucleotides. J Leukoc Biol 55, 169–174.

Chaudhuri, G. (1997). Scavenger receptor-mediated delivery of antisense mini-exon phosphorothioate oligonucleotide to Leishmania-infected macrophages. Selective and efficient elimination of the parasite. Biochem Pharmacol 53, 385–391.

Chen, P., Mayne, M., Power, C., and Nath, A. (1997). The Tat protein of HIV-1 induces tumor necrosis factor-a production: Implications for HIV-1 associated neurological diseases. J Biol Chem 272, 22385–22388.

Dominski, Z., and Kole, R. (1996). Effects of exon sequences on splicing of model pre-mRNA substrates in vitro. Acta Biochim Pol 43, 161–173.

Dominski, Z., and Kole, R. (1994). Identification and characterization by antisense oligonucleotides of exon and intron sequences required for splicing. Mol Cell Biol 14, 7445–7454.

Dominski, Z., and Kole, R. (1994). Identification of exon sequences involved in splice site selection. J Biol Chem 269, 23590–23596.

Dominski, Z., and Kole, R. (1991). Selection of splice sites in pre-mRNAs with short internal exons. Mol Cell Biol 11, 6075–6083.

Fauci, A. S. (1996). Host factors and the pathogenesis of HIV-induced disease. Nature 384, 529–534.

Ffrench-Constant, C. (1994). Pathogenesis of Multiple Sclerosis. Lancet 343, 271–275.

Gao, W. Y., Han, F. S., Storm, C., Egan, W., and Cheng, Y. C. (1992). Phosphorothioate oligonucleotides are inhibitors of human DNA polymerases and RNase H: implications for antisense technology. Mol Pharmacol 41, 223–229.

Gearing, A. J., Beckett, P., Christodoulou, M., Churchill, M., Clements, J. M., Crimmin, M., Davidson, A. H., Drummond, A. H., Galloway, W. A., Gilbert, R., and et al. (1995). Matrix metalloproteinases and processing of pro-TNF-alpha. J Leukoc Biol 57, 774–777.

Givner, L. B., Gray, L., and T M, O. S. (1995). Antibodies to tumor necrosis factor-alpha: use as adjunctive therapy in established group B streptococcal disease in newborn rats. Pediatr Res 38, 551–554.

Gough, N. (1988). Rapid and quantitative preparation of cytoplasmic RNA from small numbers of cells. Anal Biochem 173, 93–95.

Hanecak, R., Brown Driver, V., Fox, M. C., Azad, R. F., Furusako, S., Nozaki, C., Ford, C., Sasmor, H., and Anderson, K. P. (1996). Antisense oligonucleotide inhibition of hepatitis C virus gene expression in transformed hepatocytes. J Virol 70, 5203–5212.

Hartmann, G., Krug, A., Eigler, A., Moeller, J., Murphy, J., Albrecht, R., and Endres, S. (1996). Specific suppression of human tumor necrosis factor-alpha synthesis by antisense oligodeoxynucleotides. Antisense Nucleic Acid Drug Dev 6, 291–299.

Hartmann, G., Krug, A., Waller Fontaine, K., and Endres, S. (1996). Oligodeoxynucleotides enhance lipopolysaccharide-stimulated synthesis of tumor necrosis factor: dependence on phosphorothioate modification and reversal by heparin. Mol Med 2, 429–438.

Hawkins, J. D. (1988). A survey on intron and exon lengths. Nucleic Acids Res 16, 9893–9908.

Hertel, K. J., Lynch, K. W., and Maniatis, T. (1997). Common themes in the function of transcription and splicing enhancers. Curr Opin Cell Biol 9, 350–357.

Hodges, D., and Crooke, S. T. (1995). Inhibition of splicing of wild-type and mutated luciferase-adenovirus pre-mRNAs by antisense oligonucleotides. Mol Pharmacol 48, 905–918.

Iversen, P. L., Zhu, S., Meyer, A., and Zon, G. (1992). Cellular uptake and subcellular distribution of phosphorothioate oligonucleotides into cultured cells. Antisense Res Dev 2, 211–222.

Jacobson, A. B., and Zuker, M. (1993). Structural analysis by energy dot plot of a large mRNA. J Mol Biol 233, 261–269.

Khaled, Z., Benimetskaya, L., Zeltser, R., Khan, T., Sharma, H. W., Narayanan, R., and Stein, C. A. (1996). Multiple mechanisms may contribute to the cellular anti-adhesive effects of phosphorothioate oligodeoxynucleotides. Nucleic Acids Res 24, 737–745.

Khoury, G., Gruss, P., Dhar, R., and Lai, C. J. (1979). Processing and expression of early SV40 mRNA: a role for RNA conformation in splicing. Cell 18, 85–92.

Krieg, A. M., Matson, S., Cheng, K., Fisher, E., Koretzky, G. A., and Koland, J. G. (1997). Identification of an oligodeoxynucleotide sequence motif that specifically inhibits phosphorylation by protein tyrosine kinases. Antisense Nucleic Acid Drug Dev 7, 115–123.

Krieg, A. M., Matson, S., and Fisher, E. (1996). Oligodeoxynucleotide modifications determine the magnitude of B cell stimulation by CpG motifs. Antisense Nucleic Acid Drug Dev 6, 133–139.

Lappalainen, K., Miettinen, R., Kellokoski, J., Jaaskelainen, I., and Syrjanen, S. (1997). Intracellular distribution of oligonucleotides delivered by cationic liposomes: light and electron microscopic study. J Histochem Cytochem 45, 265–274.

Laptev, A. V., Lu, Z., Colige, A., and Prockop, D. J. (1994). Specific inhibition of expression of a human collagen gene (COL1A1) with modified antisense oligonucleotides. The most effective target sites are clustered in double-stranded regions of the predicted secondary structure for the mRNA. Biochemistry 33, 11033–11039.

Lefebvre d'Hellencourt, C., Diaw, L., Cornillet, P., and Guenounou, M. (1996). Inhibition of human TNF alpha and LT in cell-free extracts and in cell culture by antisense oligonucleotides. Biochim Biophys Acta 1317, 168–174.

Liang, W. W., Shi, X., Deshpande, D., Malanga, C. J., and Rojanasakul, Y. (1996). Oligonucleotide targeting to alveolar macrophages by mannose receptor-mediated endocytosis. Biochim Biophys Acta 1279, 227–234.

Lima, W. F., Monia, B. P., Ecker, D. J., and Freier, S. M. (1992). Implication of RNA structure on antisense oligonucleotide hybridization kinetics. Biochemistry 31, 12055–12061.

Lupia, E., Montrucchio, G., Battaglia, E., Modena, V., and Camussi, G. (1996). Role of tumor necrosis factor-alpha and platelet-activating factor in neoangiogenesis induced by synovial fluids of patients with rheumatoid arthritis. Eur J Immunol 26, 1690–1694.

Miraglia, L., Geiger, T., Bennett, F., and Dean, N. (1996). Inhibition of interleukin-1 type 1 receptor expression in human cell-lines by an antisense phosphorothioate oligodeoxynuclotide. Int. J. Immunopharmac. 18, 227–240.

Mishra, R. K., Le Tinevez, R., and Toulme, J. J. (1996). Targeting nucleic acid secondary structures by antisense oligonucleotides designed through in vitro selection. Proc Natl Acad Sci U S A 93, 10679–10684.

Mishra, R. K., and Toulme, J. J. (1994). In vitro selection of antisense oligonucleotides targeted to a hairpin structure. C R Acad Sci III 317, 977–982.

Moreland, L. W., Baumgartner, S. W., Schiff, M. H., Tindall, E. A., Fleishmann, R. M., Weaver, A. L., Ettlinger, R. E., Cohen, S., Koopman, W. J., Mohler, K., Widmer, M. B., and Blosch, C. M. (1997). Treatment of Rheumatoid Arthritis with a recombinant human tumor necrosis factor receptor (p75)-Fc fusion protein. N Engl J Med 337, 141–147.

Moulds, C., Lewis, J. G., Froehler, B. C., Grant, D., Huang, T., Milligan, J. F., Matteucci, M. D., and Wagner, R. W. (1995). Site and mechanism of antisense inhibition by C-5 propyne oligonucleotides. Biochemistry 34, 5044–5053.

Padgett, R. A., Grabowski, P. J., Konarska, M. M., Seiler, S., and Sharp, P. A. (1986). Splicing of messenger RNA precursors. Annu Rev Biochem 55, 1119–1150.

Perez, J. R., Li, Y., Stein, C. A., Majumder, S., van Oorschot, A., and Narayanan, R. (1994). Sequence-independent induction of Sp1 transcription factor activity by phosphorothioate oligodeoxynucleotides. Proc Natl Acad Sci U S A 91, 5957–5961.

Pfeffer, K., Matsuyama, T., Kundig, T. M., Wakeham, A., Kishihara, K., Shahinian, A., Wiegmann, K., Ohashi, P. S., Kronke, M., and Mak, T. W. (1993). Mice deficient for the 55 kd tumor necrosis factor receptor are resistant to endotoxic shock, yet succumb to L. monocytogenes infection. Cell 73, 457–467.

Power, C., McArthur, J. C., Johnson, R. T., Griffin, D. E., Glass, J. D., Dewey, R., and Chesebro, B. (1995). Distinct HIV-1 env sequences are associated with neurotropism and neurovirulence. Curr Top Microbiol Immunol 202, 89–104.

Probert, L., Akassoglou, K., Kassiotis, G., Pasparakis, M., Alexopoulou, L., and Kollias, G. (1997). TNF-alpha transgenic and knockout models of CNS inflammation and degeneration. J Neuroimmunol 72, 137–141.

Probert, L., Akassoglou, K., Pasparakis, M., Kontogeorgos, G., and Kollias, G. (1995). Spontaneous inflammatory demyelinating disease in transgenic mice showing central nervous system-specific expression of tumor necrosis factor alpha. Proc Natl Acad Sci U S A 92, 11294–11298.

Rojanasakul, Y., Weissman, D. N., Shi, X., Castranova, V., Ma, J. K., and Liang, W. (1997). Antisense inhibition of silica-induced tumor necrosis factor in alveolar macrophages. J Biol Chem 272, 3910–3914.

Selmaj, K., Raine, C. S., and Cross, A. H. (1991). Anti-tumor necrosis factor therapy abrogates autoimmune demyelination. Ann Neurol 30, 694–700.

Sharief, M. K., and Hentges, R. (1991). Association between tumor necrosis factor-alpha and disease progression in patients with multiple sclerosis. N Engl J Med 325, 467–472.

Staley, J. P., and Guthrie, C. (1998). Mechanical devices of the spliceosome: Motors, clocks, springs and things. Cell 92, 315–326.

Stein, C. A., and Cheng, Y. C. (1993). Antisense oligonucleotides as therapeutic agents—is the bullet really magical? Science 261, 1004–1012.

Talley, A. K., Dewhurst, S., Perry, S. W., Dollard, S. C. , Gummuluru, S., Fine, S. M., New, D., Epstein, L. G., Gendelman, H. E., and Gelbard, H. A. (1995). Tumor necrosis factor alpha-induced apoptosis in human neuronal cells: protection by the antioxidant N-acetylcysteine and the genes bcl-2 and crmA. Mol-Cell-Biol 15, 2359–2366.

Tarn, W. Y., and Steitz, J. A. (1997). Pre-mRNA splicing: the discovery of a new spliceosome doubles the challenge. Trends Biochem Sci 22, 132–137.

Taylor, M. F., Paulauskis, J. D., Weller, D. D., and Kobzik, L. (1996). In vitro efficacy of morpholino-modified antisense oligomers directed against tumor necrosis factor-alpha mRNA. J Biol Chem 271, 17445–17452.

Thierry, A. R., Rahman, A., and Dritschilo, A. (1993). Overcoming multidrug resistance in human tumor cells using free and liposomally encapsulated antisense oligodeoxynucleotides. Biochem Biophys Res Commun 190, 952–960.

Tomioka, H., Maw, W. W., Sato, K., and Saito, H. (1996). The role of tumour necrosis factor-alpha in combination with interferon-gamma or interleukin-1 in the induction of immunosuppressive macrophages because of Mycobacterium avium complex infection. Immunology 88, 61–67.

Tracey, K. J., and Cerami, A. (1994). Tumor necrosis factor: a pleiotropic cytokine and therapeutic target. Annu Rev Med 45, 491–503.

Uhlmann, E., Ryte, A., and Peyman, A. (1997). Studies on the mechanism of stabilization of partially phosphorothioated oligonucleotides against nucleolytic degradation. Antisense Nucleic Acid Drug Dev 7, 345–350.

Wagner, R. (1994). Gene inhibition using antisense oligonucleotides. Nature 372, 333–335.

Wang, A. M., Creasey, A. A., Ladner, M. B., Lin, L. S., Strickler, J., Van Arsdell, J. N., Yamamoto, R., and Mark, D. F. (1985). Molecular cloning of the complementary DNA for human tumor necrosis factor. Science 228, 149–154.

Wesselingh, S. L., Power, C., Glass, J. D., Tyor, W. R., McArthur, J. C., Farber, J. M., Griffin, J. W., and Griffin, D. E. (1993). Intracerebral cytokine messenger RNA expression in acquired immunodeficiency syndrome dementia. Ann Neurol 33, 576–582.

Yagi, K., Noda, H., Kurono, M., and Ohishi, N. (1993). Efficient gene transfer with less cytotoxicity by means of cationic multilamellar liposomes. Biochem Biophys Res Commun 196, 1042–1048.

Yang, Y., Yelavarthi, K. K., Chen, H. L., Pace, J. L., Terranova, P. F., and Hunt, J. S. (1993). Molecular, biochemical, and functional characteristics of tumor necrosis factor-alpha produced by human placental cytotrophoblastic cells. J Immunol 150, 5614–5624.

Zelphati, O., and Szoka, F. C., Jr. (1996). Intracellular distribution and mechanism of delivery of oligonucleotides mediated by cationic lipids. Pharm Res 13, 1367–1372.

Zheng, Z. M., and Specter, S. (1996). Dynamic production of tumour necrosis factor alpha (TNF-alpha) messenger RNA, intracellular and extracellular TNF-alpha by murine macrophages and possible association with protein tyrosine phosphorylation of STAT1 alpha and ERK2 as an early signal. Immunology 87, 544–550.

Akhter et al, 1991. Interactions of antisense DNA oligonucleotide analogs with phospholipid membranes (liposomes). Nuc. Res. 19:5551–5559.

Crooke, 1995. Progress in antisense therapeutics, Hematol. Pathol. 2:59.

Loke et al, 1989. Characterization of oligonucleotide transport into living cells. PNAS USA 86:3474.

Morrison, 1991. Suppression of basic fibroblast growth factor expression by antisense oligonucleotides inhibits the growth of transformed human astrocytes. J. Biol. Chem. 266:728.

Culver, 1998. Site-Directed recombination for repair of mutations in the human ADA gene. (Abstract) Antisense DNA & RNA based therapeutics, February, 1998, Coronado, Calif.

What is claimed is:

1. A pharmaceutical or medical composition comprising as active ingredient at least one synthetic nuclease resistant antisense oligodeoxynucleotide having a nucleotide sequence selected from the group consisting of SEQ. ID No.4 and SEQ. ID No. 6 in a physiologically acceptable carrier or diluent for delivery in vitro.

2. The pharmaceutical composition of a synthetic nuclease resistant antisense oligodeoxynucleotide comprising either SEQ. ID No. 4 or SEQ. ID No. 6 and at least one other non-control AS—ODN selected from Tables 1 and 2 wherein a percent inhibition is greater than 25%.

3. A pharmaceutical composition for selectively inhibiting mammalian tumor necrosis factor alpha in vitro consisting of;
   an effective amount of at least one active ingredient a synthetic nuclease resistant antisense oligodeoxynucleotide having a nucleotide sequence selected from the group consisting of SEQ. ID No. 4 and SEQ. ID No. 6 in a pharmaceutically physiologically acceptable carrier or diluent.

4. A pharmaceutical or medical composition comprising as active ingredient at least one synthetic nuclease resistant antisense oligodeoxynucleotide for selectively inhibiting human tumor necrosis factor-alpha in vitro, said antisense oligonucleotide comprising an exon targeting sequence flanking donor splice sites thereby regulating expression of TNF-α wherein the nucleotide sequence is selected from the group consisting of SEQ ID No: 4 and SEQ ID No: 6 in a physiologically acceptable carrier or diluent.

5. A DNA expression sequence comprising a transcriptional initiation region and a sequence encoding an oligodnucleotide as set forth in claim 3.

6. A vector comprising a DNA sequence according to claim 5.

* * * * *

SEQUENCE LISTING

```
<160> NUMBER OF SEQ ID NOS: 33

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:synthetic

<400> SEQUENCE: 1
gccagctcca cgtcccggat catgctttca                                          30

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:synthetic

<400> SEQUENCE: 2
ggctgaggaa caagcaccgc ctggag                                              26

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:synthetic

<400> SEQUENCE: 3
gactcttccc tctgggggcc gatcactcca                                          30

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence:synthetic

<400> SEQUENCE: 4
ctgactgcct gggccagagg gctgattag                                           29

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:synthetic

<400> SEQUENCE: 5
tcggggttcg agaagatgat ctgactgc                                            28
```

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:synthetic

<400> SEQUENCE: 6
ccacatgggc tacaggcttg tcactcg                                    27

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:synthetic

<400> SEQUENCE: 7
gcttgagggt ttgctacaac atgggctaca                                 30

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:synthetic

<400> SEQUENCE: 8
ggcccggcgg ttcagccact ggag                                       24

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:synthetic

<400> SEQUENCE: 9
cacgccattg gccaggaggg cattgg                                     26

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:synthetic

<400> SEQUENCE: 10
aggtacaggc cctctgatgg caccaccag                                  29

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:synthetic

<400> SEQUENCE: 11
cctgtcttct tggggagcgc ctcctc                                     26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:synthetic

<400> SEQUENCE: 12
ctggggcccc cctgtcttct tgggga                    26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:synthetic

<400> SEQUENCE: 13
gcctggagcc ctggggcccc cctgtc                    26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:synthetic

<400> SEQUENCE: 14
acaaagcacc gcctggagcc ctgggg                    26

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:synthetic

<400> SEQUENCE: 15
ggaaggagaa gaggctgagg aaca                      24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:synthetic

<400> SEQUENCE: 16
tgccacgatc aggaaggaga a                         21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:synthetic

<400> SEQUENCE: 17
gcagcaggaa gaagagcgtg gtg                       23

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:synthetic

<400> SEQUENCE: 18
aataataaat aaataataaa taatcacaag                30

<210> SEQ ID NO 19

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence:synthetic

<400> SEQUENCE: 19
catgctttca gtcat                                                    15

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence:synthetic

<400> SEQUENCE: 20
tgtgctcatg gtgtctttt                                                18

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:synthetic

<400> SEQUENCE: 21
ctgacatcct gggccccagg gctgattag                                     29

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:synthetic

<400> SEQUENCE: 22
ctgactgcct gctccagagg gctgatt                                       27

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:synthetic

<400> SEQUENCE: 23
atcgtccgga tctgtctctg t                                             21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:synthetic

<400> SEQUENCE: 24
gattagagag aggtccctgg g                                             21

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence:synthetic

<400> SEQUENCE: 25
tgggccagag ggctga                                                   16

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence:synthetic

<400> SEQUENCE: 26
agggctgatt agagagaggt c                                             21

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:synthetic

<400> SEQUENCE: 27
tgcctgggcc agagggctga ttag                                          24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence:synthetic

<400> SEQUENCE: 28
ctgactgcct gggccagagg gctg                                          24

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:synthetic

<400> SEQUENCE: 29
actgcctggg ccagagggct g                                             21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence:synthetic

<400> SEQUENCE: 30
ttcgagaaga tgatctgact g                                             21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence:synthetic

<400> SEQUENCE: 31
gaagatgatc tgactgcctg g                                             21

<210> SEQ ID NO 32
<211> LENGTH: 18
<212> TYPE: DNA

-continued

```
<213> ORGANISM: Artificial Sequence
<220> FEATURE:
<223> OTHER INFORMATION: Description of Artificial Sequence:synthetic

<400> SEQUENCE: 32
ggggttcgag aagatgat                                                  18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence:synthetic

<400> SEQUENCE: 33
cttgtcactc ggggttcg                                                  18
```